(12) United States Patent
Thramann et al.

(10) Patent No.: US 7,427,294 B2
(45) Date of Patent: *Sep. 23, 2008

(54) SPINAL IMPLANT

(75) Inventors: Jeffery Thramann, Longmont, CO (US); Michael Fulton, Superior, CO (US)

(73) Assignee: Lanx, Inc., Broomfield, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/318,993

(22) Filed: Dec. 27, 2005

(65) Prior Publication Data

US 2006/0136059 A1 Jun. 22, 2006

Related U.S. Application Data

(63) Continuation-in-part of application No. 10/680,982, filed on Oct. 7, 2003, now Pat. No. 7,041,137.

(51) Int. Cl.
*A61F 2/44* (2006.01)
(52) U.S. Cl. .................................... 623/17.11
(58) Field of Classification Search .... 623/17.11–17.16
See application file for complete search history.

(56) References Cited

U.S. PATENT DOCUMENTS

| | | | |
|---|---|---|---|
| 4,834,757 A | 5/1989 | Brantigan | |
| 5,425,772 A | 6/1995 | Brantigan | |
| 5,443,514 A | 8/1995 | Steffee | |
| 5,658,336 A | 8/1997 | Pisharodi | |
| 5,702,449 A | 12/1997 | McKay | |
| 5,716,415 A | 2/1998 | Steffee | |
| 5,766,252 A | 6/1998 | Henry et al. | |
| 5,865,845 A | 2/1999 | Thalgott | |
| 5,888,227 A | 3/1999 | Cottle | |
| 6,045,580 A | 4/2000 | Scarborough et al. | |
| 6,102,950 A | 8/2000 | Vaccaro | |
| 6,240,926 B1 | 6/2001 | Chin Gan et al. | |
| 6,241,771 B1 | 6/2001 | Gresser et al. | |
| 6,245,108 B1 | 6/2001 | Biscup | |
| 6,258,125 B1 | 7/2001 | Paul et al. | |
| 6,277,149 B1 | 8/2001 | Boyle et al. | |
| 6,287,343 B1 | 9/2001 | Kuslich et al. | |
| 6,350,283 B1 * | 2/2002 | Michelson | 623/17.11 |
| 6,413,278 B1 | 7/2002 | Marchosky | |
| 6,416,551 B1 | 7/2002 | Keller | |
| 6,447,544 B1 | 9/2002 | Michelson | |
| 6,458,159 B1 | 10/2002 | Thalgott | |
| 6,827,740 B1 | 12/2004 | Michelson | |
| 6,843,805 B2 | 1/2005 | Webb et al. | |
| 7,041,137 B2 * | 5/2006 | Fulton et al. | 623/17.11 |
| 2001/0008980 A1 | 7/2001 | Gresser et al. | |
| 2001/0039453 A1 | 11/2001 | Gresser et al. | |
| 2002/0040242 A1 | 4/2002 | Picha et al. | |
| 2002/0049497 A1 | 4/2002 | Mason | |
| 2002/0087212 A1 * | 7/2002 | James et al. | 623/17.11 |
| 2003/0036798 A1 | 2/2003 | Alfaro et al. | |
| 2003/0125739 A1 | 7/2003 | Bagga et al. | |

(Continued)

*Primary Examiner*—Suzette J Gherbi
(74) *Attorney, Agent, or Firm*—Holland & Hart LLP

(57) ABSTRACT

The present invention provides an implant to be implanted between a superior vertebra and an inferior vertebra. The implant comprises a main body having a superior surface and an inferior surface with at least one linear surface protrusion residing on at least one of the superior surface or the inferior surface. The protrusion having a substantially flat bone engaging surface and a generally trapezoidal cross-section.

18 Claims, 4 Drawing Sheets

U.S. PATENT DOCUMENTS

| | | |
|---|---|---|
| 2004/0127990 A1 | 7/2004 | Bartish, Jr. et al. |
| 2005/0004671 A1 | 1/2005 | Ross et al. |
| 2005/0021144 A1* | 1/2005 | Malberg et al. .......... 623/17.11 |
| 2005/0027360 A1* | 2/2005 | Webb et al. .............. 623/17.11 |
| 2005/0055098 A1 | 3/2005 | Zdeblick et al. |
| 2005/0119753 A1 | 6/2005 | Mchan et al. |
| 2005/0216088 A1 | 9/2005 | McKinely et al. |
| 2005/0256574 A1 | 11/2005 | Paul et al. |
| 2005/0261771 A1 | 11/2005 | Paul et al. |

* cited by examiner

SPINAL IMPLANT

RELATED APPLICATION

This application is a continuation-in-part of U.S. patent application Ser. No. 10/680,982, titled SPINAL IMPLANT, filed Oct. 7, 2003, now U.S. Pat. No. 7,041,137.

FIELD OF THE INVENTION

The present invention relates to apparatuses and methods for implanting a device in the intervertebral space and, more particularly, to an allograft spinal implant.

BACKGROUND OF THE INVENTION

The vertebrae of the human spine are arranged in a column with one vertebra on top of the next. Between each vertebra exists an intervertebral disc that transmits force between adjacent vertebrae and provides a cushion between the adjacent vertebrae.

Sometimes, back pain is caused by degeneration or other deformity of the intervertebral disc ("diseased disc"). Conventionally, surgeons treat diseased discs by surgically removing the diseased disc and inserting a bone graft in the space vacated by the diseased disc. The adjacent vertebrae are then immobilized relative to one another. Eventually, the vertebrae grow into one solid piece of bone.

A variety of different types of bone grafts, also known as intervertebral implants, have been developed to assist in bone growth. These bone grafts can be made out of a number of biocompatible materials, such as, for example, ceramics, metals, bone, and the like. All the various known bone grafts, however, have one or more drawbacks that make the various bone grafts more or less desirable depending on the circumstances.

Accordingly, a need exists for an improved spinal implant.

SUMMARY OF THE INVENTION

To attain the advantages and in accordance with the purpose of the invention, as embodied and broadly described herein, a spinal implant is provided. The spinal implant comprises a main body. The main body has a superior face and an inferior face, each designed with protrusions, to engage superior and inferior vertebral bodies. The main body further comprises an anterior end and a posterior end. The anterior end and posterior end can connected by a straight or curved sidewall. Alternatively, the anterior end and posterior end can be defined portions of a circular sidewall connecting the superior face and the inferior face.

The foregoing and other features, utilities and advantages of the invention will be apparent from the following more particular description of a preferred embodiment of the invention as illustrated in the accompanying drawings. Further, the advantages and purpose of the invention will be realized and attained by means of the elements and combinations particularly pointed out in the appended claims.

BRIEF DESCRIPTION OF THE DRAWING

The accompanying drawings, which are incorporated in and constitute a part of this specification, illustrate embodiments of the present invention, and together with the description, serve to explain the principles thereof. Like items in the drawings are referred to using the same numerical reference.

DETAILED DESCRIPTION

Figure 1:
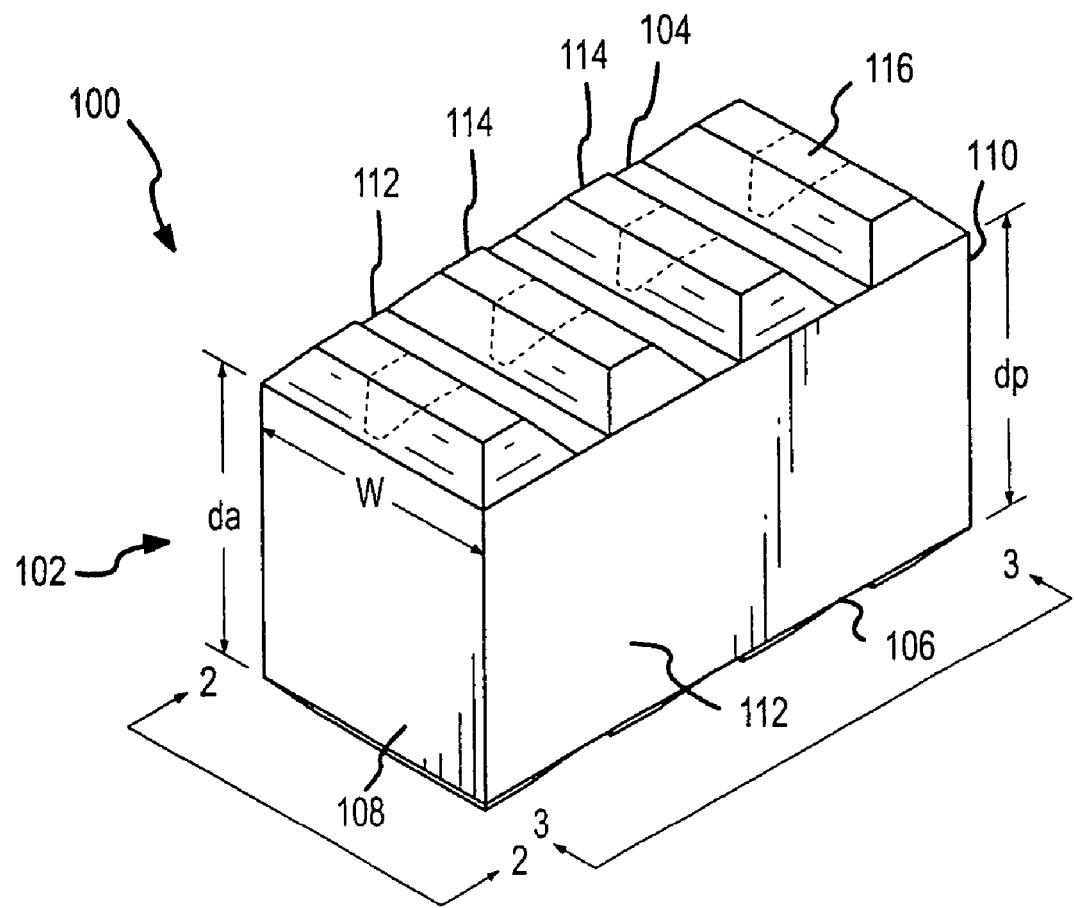
FIG. 1 shows a front perspective view of a spinal implant constructed in accordance with an embodiment of the present invention.

Some embodiments of the present invention are described with reference to FIGS. 1 to 11. FIGS. 1 to 11 are not shown to scale and should be considered exemplary rather than limiting. Referring first to FIGS. 1 to 4, a spinal implant 100 consistent with the present invention is shown. It is contemplated that spinal implants consistent with the present invention could be constructed out of a number of different materials, such as, for example, bone, biocompatible metals, plastics, ceramics, and other synthetics, which may or may not be resorbable. Spinal implant 100 comprises a main body 102 having a superior surface 104, an inferior surface 106, an anterior surface 108, a posterior surface 110, and sidewalls 112 connecting the various surfaces. Extending from the superior surface 104 and the inferior surface 106 exist a plurality of linear ridges 114. One or more linear ridges 114 could extend a majority of the width W of the implant 100 or, alternatively, one or more channels 116 (shown in phantom) could separate linear ridges 114 into two or more serial ridges. Each ridge 114 could have the same or a different number of optional channels. Further, while the figures are not drawn to scale, it is generally desirable to mill ridges 114 such that a majority of superior surface 104 and inferior surface 106 have ridges.

Figure 2:
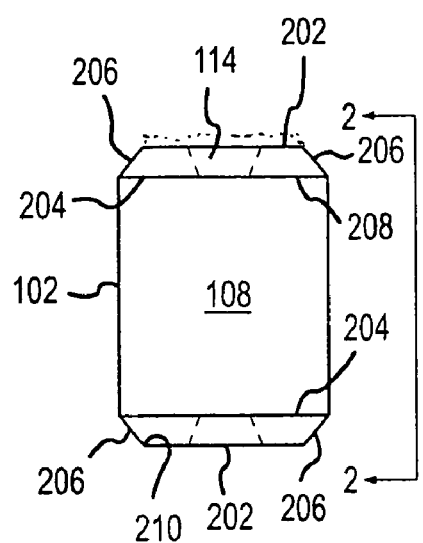
FIG. 2 shows a front elevation view of the spinal implant of FIG. 1.
Figure 3:
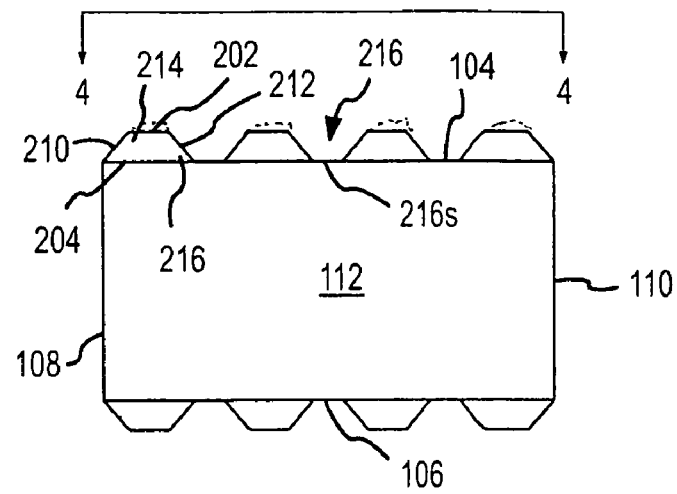
FIG. 3 shows a side elevation view of the spinal implant of FIG. 1.
Figure 4:
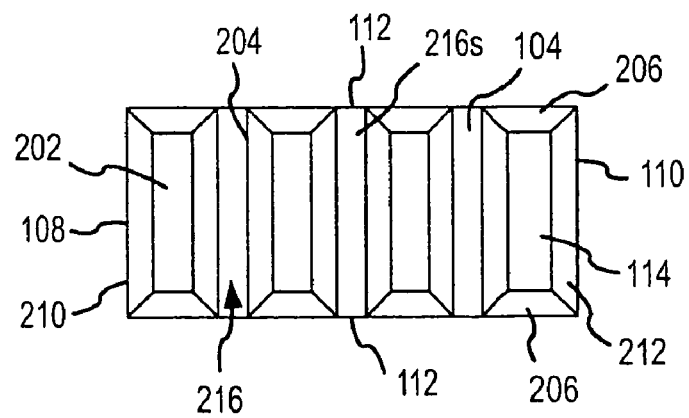
FIG. 4 shows a top elevation view of the spinal implant of FIG. 1.

Referring now to FIGS. 2 to 4, ridges 114 will be explained in more detail. As shown in FIG. 2, ridges 114 have a generally flat vertebral body engaging surface 202 and a generally flat implant engaging surface 204. As one of ordinary skill in the art would appreciate on reading the disclosure, generally flat vertebral body engaging surface 202 may be contoured to match the anatomy of the vertebral body it is engaging, which is shown in phantom on FIG. 2. Notice flat implant engaging surface 204 is shown for convenience. While ridges 114 could be individually adhered to main body 102, generally ridges 114 are milled out of or molded to main body 102 such that the main body and ridges form a single integral unit. Ridges 114 also have lateral sides 206 that extend from surface 202 to surface 204. Lateral sides 206 form an acute angle 208 with surface 204 and an obtuse angle 210 with surface 202. While lateral sides 206 are shown having equal lengths, the sides can be of different lengths providing ridges 114 with an angled or skewed appearance. FIG. 3 shows ridges 114 have an anterior side 210 and a posterior side 212. Sides 210 and 212 form an acute angle 216 with surface 204 and an obtuse angle 214 with surface 202. Similar to sides 206, sides 210 and 212 can have different lengths to angle or skew ridge 114 (See for example FIGS. 5 and 6). As shown, ridges 114 have trapezoidal cross-sections in both the anterior to posterior direction as well as the side-to-side (or lateral) direction. Also, as best seen in FIG. 4, a trough 216t resides between every two ridges 114. As shown, trough 216t is shaped similar to ridges 114, but inverted. Trough 216t and ridges 114 do not need to have identical shapes. Trough 216 has sides 210 and 212 in common with adjacent ridges 114 and a surface 216s that coincides with either superior surface 104 and/or inferior surface 106.

Figure 5:
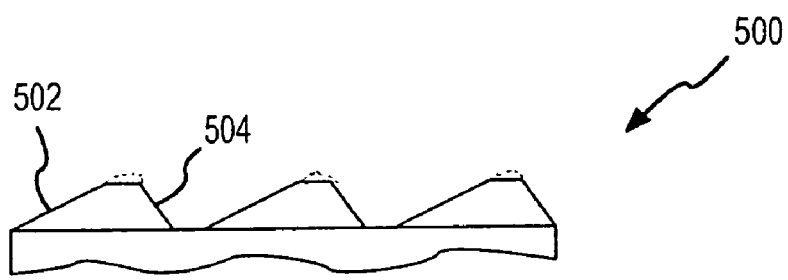
FIG. 5 shows a side elevation view of ridges for a spinal implant consistent with an embodiment of the present invention.
Figure 6:
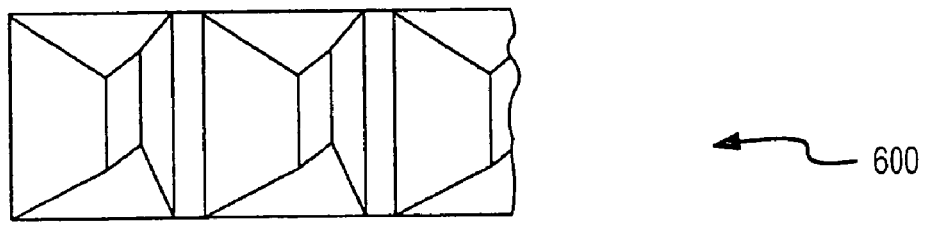
FIG. 6 shows a top elevation view of ridges for a spinal implant consistent with another embodiment of the present invention.

Referring now to FIG. 5, a side elevation view of ridges 500 is shown. Ridges 500 are similar to ridges 114, and the similarities will not be explained herein. Ridges 500 have anterior sides 502 and posterior sides 504. Unlike ridges 114, anterior sides 502 and posterior sides 504 are different lengths, providing the skewed feature. In this case, anterior side 502 is longer than posterior side 504. Alternatively, anterior side 502 could be shorter than posterior side 504. Differing the lengths of the sides should make expulsion of the implant by natural body forces more difficult. The sides would be lengthened or shortened based on design choice and the particular forces the implant is to resist. While changing the anterior and posterior side lengths would resist anterior to posterior expulsion forces, changing the lengths of sides 206 such that the implant has a longer side and a shorter side 206 would assist in resisting lateral forces. Various combinations of lengthening and shortening could produce many alternative shapes. See, for example, FIG. 6 showing ridges 600 having generally trapezoidal cross-sections in all directions, but skewed lengths.

While FIGS. 1-6 are generally described as cubic implants, alternative shapes are possible. For example, superior surface 104 and inferior surface 106 could converge on one end and diverge towards the other forming a wedge shape. In this case, generally, a distance da separating the superior surface 104 and inferior surface 106 at anterior side 108 would be larger than a distance dp separating superior surface 104 and inferior surface 106 at posterior side 110 (see FIG. 1).

Figure 7:
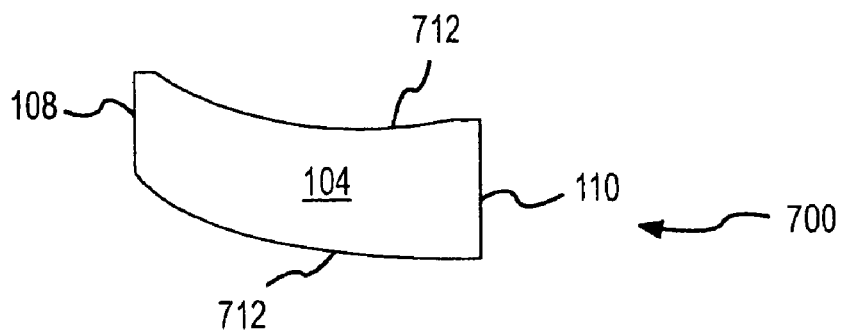
FIG. 7 shows a top elevation view of a spinal implant constructed in accordance with another embodiment of the present invention.
Figure 8:
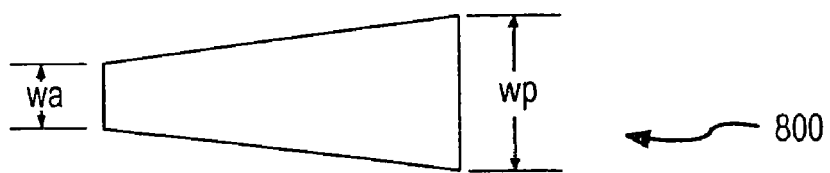
FIG. 8 shows a top elevation view of a spinal implant constructed in accordance with another embodiment of the present invention.

FIG. 7 shows an implant 700. Implant 700 is similar to implant 100, and the similarities will not be further explained, but sides 712 are curve to provide a concave shape to implant. While not specifically shown, implant 700 would have ridges similar to implant 100. FIG. 8 shows still another implant 800. In this case, implant 800 has an anterior side width dimension Wa and a posterior width dimension Wp, which forms a somewhat conical shape. Various combinations of da, dp, Wa, and Wp could be combined with parallel or substantially parallel sidewalls (FIGS. 1-4), or arched sidewalls (FIG. 7).

Figure 9:
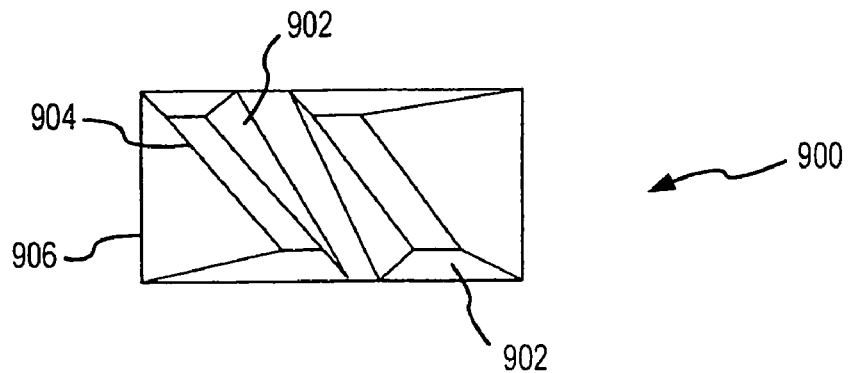
FIG. 9 shows a top elevation view of a spinal implant constructed in accordance with another embodiment of the present invention.
Figure 10:
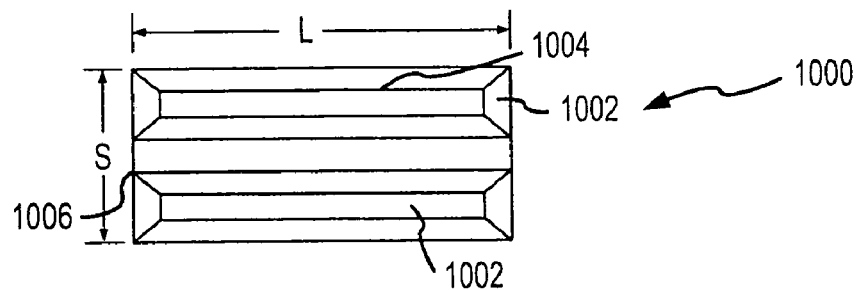
FIG. 10 shows a top elevation view of a spinal implant constructed in accordance with another embodiment of the present invention.

Generally, the spinal implants shown above are useful in the posterior lumbar interbody fusion (PLIF) and transforaminal lumbar interbody fusion (TLIF) techniques. However, using the TLIF techniques, implants are generally inserted at an angle and rotated in the intervertebral space. FIGS. 9 and 10 show top elevation views of implants 900 and 1000 useful in TLIF techniques, although implants 900 and 1000 could be used in PLIF technique as well. Referring first to FIG. 9, implant 900 has a series of surface protrusions 902. A leading edge 904 of surface protrusions 902 is angled with respect to anterior surface 906. As shown in FIG. 10, implant 1000 has a series of surface protrusions 1002. A leading edge 1004 of surface protrusion 1002 is perpendicular to side 1006, in other words, the surface protrusions are arranged along the longer dimension L of the implant rather than the shorter dimension S of the implant. Conventionally, surface protrusions are aligned along the shorter dimension S. While protrusions 902 and 1002 are shown as generally trapezoidal shapes, protrusions 902 and 1002 could be conical or triangular in shape. In other words, the bone engaging surface associated with implants 900 and 10000 could form a cutting edge instead of a flat engaging surface.

Figure 11:
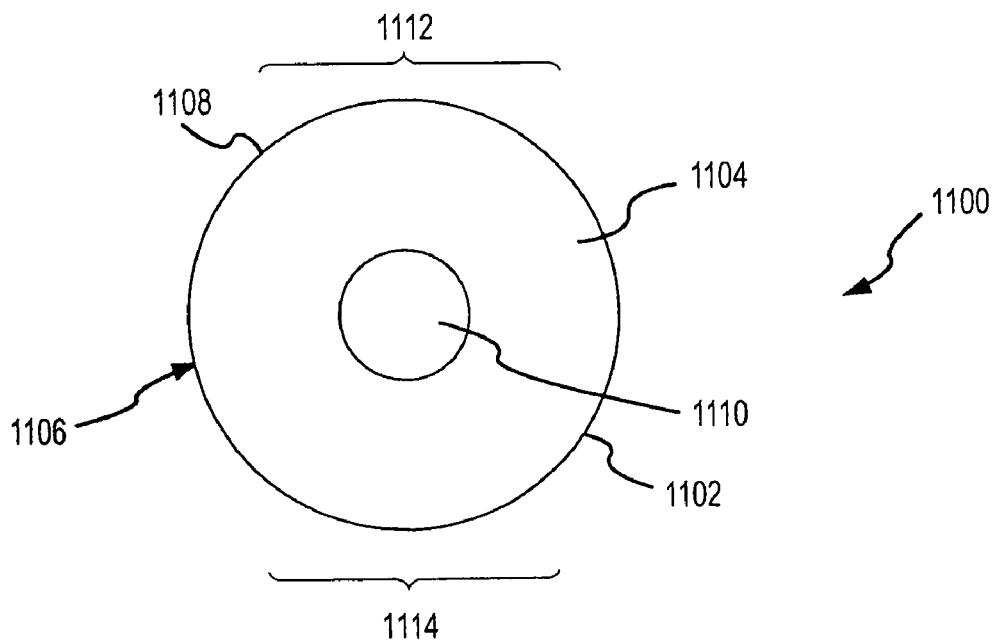
FIG. 11 shows a top elevation view of a spinal implant constructed in accordance with another embodiment of the present invention.

While usable in all spinal regions, the implants shown and described with respect to FIGS. 1 to 10 are generally used as implants for the lumbar or thorax regions of the spine. FIG. 11 shows a top elevation view of an implant 1100 more suitable for the cervical region of the spine, although implant 1100 could be used in the lumbar or thorax region as well. While not shown, implant 1100 would be milled to have surface protrusions similar to the protrusions shown in FIGS. 1-6, 9 and 10. Implant 1100 comprises a main body 1102, a superior surface 1104, an inferior surface 1106 that is generally opposite superior surface 1104, and a annular sidewall 1108 surrounding main body 1102 and connecting superior surface 1104 and inferior surface 1106. Annular sidewall 1108 is used generically and should not be limited to circular, but rather includes other geometric shapes, such as, for example, oval, elliptical, trapezoidal, or the like. A hollow region 1110 may reside internal to implant 1100 giving implant 1100 a doughnut like shape. Hollow region 1110 may be the intramedullary canal of a conventional bone. Moreover, hollow region 1110 could be milled out from a solid implant, such as a solid bone piece. Further, hollow region 1110 is used generically to mean a lack of cortical bone in the region, other substances, such as, for example, cancellous bone, may reside in region 1110. Instead of specific anterior and posterior sides, sidewall 1108 has an anterior region 1112 and a posterior region 1114. While shown as a circular cross section, implant 1100 could be flattened over posterior region 1114 or anterior region 1112 to more conform to a patient's anatomy. Further, implant 1100 could be a wedge shape with superior surface 1104 and inferior surface 1106 converging at posterior region 1114 and diverging at anterior region 1112.

While particular shapes and designs for the implants shown in FIGS. 1-11 are shown and described, one of ordinary skill in the art would recognize on reading the disclosure that other shapes and designs are possible. In particular, the implants could be cubic, oval, elliptical, triangular, trapezoidal, conical, or the like.

While the invention has been particularly shown and described with reference to some embodiment thereof, it will be understood by those skilled in the art that various other changes in the form and details may be made without departing from the spirit and scope of the invention.

We claim:

1. An implant for insertion into a space between a superior vertebra and an inferior vertebra, the implant comprising:
   a main body, the main body comprising at least a superior surface and an inferior surface;
   a plurality of surface protrusions residing on at least one of the superior surface or the inferior surface; and
   a plurality of spaces residing on at least one of the superior surface or the inferior surface separating the plurality of surface protrusions, wherein
   the plurality of surface protrusions comprise:

an anterior facing surface,
a posterior facing surface,
a plurality of laterally facing surfaces, and
a substantially planer vertebral body engaging surface, such that
the anterior facing surface and the posterior facing surface converge from the main body to the vertebral body engaging surface forming a trapezoidal cross section and the plurality of laterally facing surfaces converge from the main body to the vertebral body engaging surface forming a trapezoidal cross section; and
each of the plurality of surface protrusions including at least one channel therein.

2. The implant of claim 1, wherein the vertebral body engaging surface is substantially shaped to conform to at least one of an inferior surface of the superior vertebra or the superior surface of the inferior vertebra.

3. The implant of claim 2, wherein the implant comprises bone and wherein the plurality of linear surfaces are milled from the bone.

4. The implant of claim 2, wherein the implant comprises a biocompatible material.

5. The implant of claim 1, further comprising a plurality of troughs separating the plurality of surface protrusions.

6. The implant of claim 5, wherein the plurality of troughs reside in the plurality of spaces.

7. The implant of claim 1, further comprising at least one bore through the main body.

8. The implant of claim 1, wherein one of the anterior facing surface or the posterior facing surface is substantially vertical.

9. The implant of claim 1 wherein the anterior facing surface and the posterior facing surface converge between the plurality of laterally facing surfaces.

10. An implant for insertion into a space between a superior vertebra and an inferior vertebra, the implant comprising:
a main body, the main body comprising at least a superior surface and an inferior surface;
a plurality of surface protrusions residing on at least one of the superior surface or the inferior surface; and
a plurality of spaces residing on at least one of the superior surface or the inferior surface separating the plurality of surface protrusions, wherein
the plurality of surface protrusions comprise:
an anterior facing surface,
a posterior facing surface,
a plurality of laterally facing surfaces, and
a substantially planer vertebral body engaging surface shaped to substantially conform with a superior vertebra or an inferior vertebra, wherein the plurality of surface protrusions comprise a trapezoidal cross-section in an anterior, posterior, and lateral direction; and
each of the plurality of surface protrusions including at least one channel therein.

11. The implant of claim 10, wherein the implant comprises bone.

12. The implant of claim 10, wherein the implant comprises resorbable material.

13. The implant of claim 10, wherein the anterior facing surface and the posterior facing surface converge from the main body to the vertebral body engaging surface, and the plurality of laterally facing surfaces converge from the main body to the vertebral body engaging surface.

14. The implant of claim 10, further comprising at least one space residing on at least one of the superior surface or the inferior surface separating the plurality of surface protrusions.

15. The implant of claim 10, further comprising a plurality of troughs residing between the plurality of surface protrusions.

16. The implant of claim 10, wherein the main body is substantially circular.

17. The implant of claim 10, wherein the main body diverges from an anterior portion to a posterior portion.

18. An implant for insertion into a space between a superior vertebra and an inferior vertebra, the implant comprising:
a main body;
a superior surface residing on the main body and an inferior surface residing on the main body opposite the superior surface;
at least one sidewall about the main body connecting the superior surface and the inferior surface;
an anterior region residing on the main body and a posterior region residing on the main body opposite the anterior region and connected by the at least one sidewall;
a plurality of linear surface protrusions residing on at least one of the superior surface and the inferior surface, the linear surface protrusions comprising:
an anterior facing surface,
a posterior facing surface,
a plurality of laterally facing surfaces,
a substantially flat main body engaging surface,
a substantially planer and flat bone engaging surface opposite the main body engaging surface, and
the anterior facing surface and the posterior facing surface converging between the substantially flat main body engaging surface to the substantially planer and flat bone engaging surface and the plurality of laterally facing surfaces converging between the substantially flat main body engaging surface to the substantially planer and flat bone engaging surface, such that
the linear surface protrusion has a generally trapezoidal cross-section in both an anterior to posterior direction and a lateral direction; and
each of the plurality of linear surface protrusions including at least one channel therein.

* * * * *